US010716499B1

(12) United States Patent
Freeman

(10) Patent No.: US 10,716,499 B1
(45) Date of Patent: Jul. 21, 2020

(54) PHYSIOLOGICAL MONITORING BY OPTICAL SPECTROSCOPY

(71) Applicant: ZOLL Medical Corporation, Chelmsford, MA (US)

(72) Inventor: Gary Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 980 days.

(21) Appl. No.: 15/079,020

(22) Filed: Mar. 23, 2016

Related U.S. Application Data

(60) Provisional application No. 62/137,731, filed on Mar. 24, 2015.

(51) Int. Cl.
| | | |
|---|---|---|
| *A61B 5/1455* | (2006.01) | |
| *A61B 5/1459* | (2006.01) | |
| *A61B 5/145* | (2006.01) | |
| *A61B 5/01* | (2006.01) | |
| *A61B 5/00* | (2006.01) | |
| *A61B 5/026* | (2006.01) | |
| *A61B 5/1495* | (2006.01) | |
| *A61B 17/34* | (2006.01) | |

(Continued)

(52) U.S. Cl.
CPC .............. *A61B 5/1459* (2013.01); *A61B 5/01* (2013.01); *A61B 5/0261* (2013.01); *A61B 5/031* (2013.01); *A61B 5/1495* (2013.01); *A61B 5/14532* (2013.01); *A61B 5/14535* (2013.01); *A61B 5/14539* (2013.01); *A61B 5/14546* (2013.01); *A61B 5/14552* (2013.01); *A61B 5/14553* (2013.01); *A61B 5/14556* (2013.01); *A61B 5/4875* (2013.01); *A61B 5/6852* (2013.01); *A61B 17/1691* (2013.01); *A61B 17/3468* (2013.01); *A61B 2562/0238* (2013.01); *A61B 2562/0242* (2013.01)

(58) Field of Classification Search
CPC ....... A61B 5/1459; A61B 5/01; A61B 5/0261; A61B 5/14532; A61B 5/14535; A61B 5/14539; A61B 5/14546; A61B 5/14552; A61B 5/14553; A61B 5/14556; A61B 5/1495; A61B 5/4875; A61B 5/6852; A61B 17/1691; A61B 17/3468; A61B 2562/0238; A61B 2562/0242
See application file for complete search history.

(56) References Cited

U.S. PATENT DOCUMENTS

| | | | | |
|---|---|---|---|---|
| 5,024,226 A | * | 6/1991 | Tan ........................ | A61B 5/031 600/340 |
| 5,579,774 A | * | 12/1996 | Miller .................... | A61B 5/031 600/479 |
| 5,931,779 A | | 8/1999 | Arakaki et al. | |

(Continued)

OTHER PUBLICATIONS

Wilson, J.R. et al., "Noninvasive Detection of Skeletal Muscle Underperfusion with Near-Infrared Spectroscopy in Patients with Heart Failure," Circulation, vol. 80, No. 6, pp. 1668-1674, Dec. 1989.

(Continued)

*Primary Examiner* — Eric F Winakur
(74) *Attorney, Agent, or Firm* — Fish & Richardson P.C.

(57) ABSTRACT

Optical spectroscopic devices, apparatus, systems and methods useable for physiological monitoring from intraosseous, subosseous, epidural, subdural, intraventricular, intramuscular, sub-adipose and other subcutaneous locations.

20 Claims, 11 Drawing Sheets

(51) Int. Cl.
*A61B 17/16* (2006.01)
*A61B 5/03* (2006.01)

(56) References Cited

U.S. PATENT DOCUMENTS

| | | | |
|---|---|---|---|
| 6,212,424 B1 | 4/2001 | Robinson | |
| 6,990,364 B2 | 1/2006 | Ruchti et al. | |
| 7,120,481 B2* | 10/2006 | Keller | A61B 5/0261 600/339 |
| 7,245,373 B2 | 7/2007 | Soller et al. | |
| 7,608,097 B2* | 10/2009 | Kyle | A61B 17/7098 606/304 |
| 7,613,489 B2 | 11/2009 | Myers | |
| 7,647,092 B2 | 1/2010 | Motz et al. | |
| 8,277,385 B2 | 10/2012 | Berka et al. | |
| 8,346,329 B2 | 1/2013 | Xu et al. | |
| 8,406,838 B2 | 3/2013 | Kato | |
| 8,649,849 B2 | 2/2014 | Liu et al. | |
| 2006/0100489 A1* | 5/2006 | Pesach | A61B 5/0059 600/310 |
| 2006/0253007 A1* | 11/2006 | Cheng | A61B 5/0048 600/310 |
| 2007/0265513 A1* | 11/2007 | Schenkman | A61B 5/0059 600/363 |
| 2010/0217196 A1* | 8/2010 | Nelson | A61M 5/141 604/174 |
| 2011/0184683 A1 | 7/2011 | Soller et al. | |
| 2011/0201962 A1* | 8/2011 | Grudic | A61B 5/021 600/561 |
| 2013/0225955 A1 | 8/2013 | Schenkman et al. | |
| 2014/0024904 A1 | 1/2014 | Takinami | |
| 2014/0135647 A1 | 5/2014 | Wolf, II | |

OTHER PUBLICATIONS

McKinley, Bruce A., et al., "Tissue Hemoglobin O2 Saturation during Resuscitation of Traumatic Shock Monitored Using Near Infrared Spectrometry," Journal of Trauma and Acute Care Surgery, vol. 48, Issue 4, pp. 637-642, Apr. 2000.

Frisch, A., et al., "Potential Utility of Near-Infrared Spectroscopy in Out-of-Hospital Cardiac Arrest: An Illustrative Case Series," Prehospital Emergency Care, vol. 16, No. 4, pp. 564-570, 2012.

Booth, E.A. et al., "Near-Infrared Spectroscopy Monitoring of Cerebral Oxygen During Assisted Ventilation," Surgical Neurology International, No. 2, p. 65, 2011.

M. Mullner et al., "Near Infrared Spectroscopy During and After Cardiac Arrest—Preliminary Results," Clinical Intensive Care, vol. 6, No. 3, pp. 107-111 (1995), Abstract.

Bhunia, S. K. et al., "Implanted Near-Infrared Spectroscopy for Cardiac Monitoring", Proc. SPIE 7896, Optical Tomography and Spectroscopy of Tissue IX, 789632 (2011). [http://proceedings.spiedigitallibrary.org/proceeding.aspx?articleid=733147].

Strong, E.B., et al., "Calvarial Bone Graft Harvest: A New Technique," Otolaryngology—Head and Neck Surgery, vol. 123, Issue 5, pp. 547-552. , Nov. 2000.

Yoshimura, Y., et al., "An Instrument for Harvesting the Outer Table of the Skull," Journal of Craniomaxillofacial Surgery, vol. 18, No. 4, pp. 179-181, May 1990.

Yamakawa, Toshitaka et al., "Development of an Implantable Flexible Probe for Simultaneous Near-Infrared Spectroscopy and Electrocorticography," IEEE Transactions on Biomedical Engineering, vol. 61, No. 2, Feb. 2014.

Day, Michael W., "Intraosseous Devices for Intravascular Access in Adult Trauma Patients," Critical Care Nurse, vol. 31, No. 2, Apr. 2011.

Walsh III, Joseph A., et al., "Novel Wireless Devices for Cardiac Monitoring," Circulation, 2014;130:573-581.

* cited by examiner

PHYSIOLOGICAL MONITORING BY OPTICAL SPECTROSCOPY

RELATED APPLICATION

This application claims priority to U.S. Provisional Patent Application No. 62/137,731 entitled "Physiological Monitoring by Optical Spectroscopy" filled Mar. 24, 2015, the entire disclosure of which is expressly incorporated herein by reference.

FIELD OF THE INVENTION

The present invention relates to the fields biology, medicine and biomedical engineering and more particularly to optical spectroscopy apparatus, devices, systems and methods useable for physiological monitoring from intraosseous, subosseous, epidural, subdural, intraventricular, intramuscular, sub-adipose and other subcutaneous locations.

BACKGROUND OF THE INVENTION

Pursuant to 37 CFR 1.71(e), this patent document contains material which is subject to copyright protection and the owner of this patent document reserves all copyright rights whatsoever except where otherwise noted.

Various forms of optical spectroscopy have heretofore been used for measuring the physiologic variable in living tissue (broadly referred to herein as "Physiologic Spectroscopy" (PS)). For example, some types of optical spectroscopy, such as near infrared spectroscopy (NIRS), have been used to quickly detect changes in hemoglobin thereby sensing when blood volume or flow in a particular organ or tissue changes. Also, optical spectroscopy techniques have been used for determining pH, temperature, oxygen tension, oxygen saturation, partial pressure of oxygen, partial pressure of carbon dioxide, hemoglobin concentration, water concentration, hematocrit, glucose concentration or the presence/absence of a biomarker. In some cases, an optical dye, such as indocyanine green (ICG), can be injected and optical spectroscopy can be used to measure changes in ICG concentration at a particular location and for computing blood flow and/or metabolic rates of oxygen consumption based on those measurements.

However, the use of optical spectroscopy at internal locations within a patient's body (e.g., brain tissue including deep brain tissue, internal organs, tumors, etc.) is dependent upon whether the emitter and/or detector components of the optical spectroscopy system can be operatively positioned near enough to the desired internal location to obtain the desired measurements. PS devices positioned on the surface of the skin have only limited use for monitoring tissues located near the body surface. For example, transcutaneous NIRS devices can be used to assess skeletal muscle oxygenation ($SmO_2$) in patients with heart failure by comparing light absorption at 760 nm and 800 nm as indicia of hemoglobin-myoglobin oxygenation. Wilson, J. R. et al.; *Noninvasive Detection Of Skeletal Muscle Underperfusion With Near-Infrared Spectroscopy In Patients With Heart Failure;* Circulation, 80(6), Pages 1668-74 (1989). Also, hemoglobin oxygen saturation ($StO_2$) in skeletal muscle has been successfully measured in severely injured trauma patients deemed to be at risk of multiple organ failure using a transcutaneous NIR spectroscopy probe positioned on the surface of the skin. McKinley, Bruce A., et al.; *Tissue Hemoglobin O2 Saturation during Resuscitation of Traumatic Shock Monitored Using Near Infrared Spectrometry;* Journal of Trauma and Acute Care Surgery, Vol. 48, Issue 4, 637-642 (April 2000). However, optical spectroscopic measurements from skeletal muscle located near the skin may not be indicative of metabolic activity or oxygenation of critical internal organs or tissues for various reasons. For example peripheral blood circulation can be dramatically limited by the administration of vasopressors or vasodilators. Frisch, A., et al.; *Potential Utility of Near-Infrared Spectroscopy in Out-of-Hospital Cardiac Arrest: An Illustrative Case Series;* Prehospital Emergency Care, Vol. 16, No. 4: Pages 564-570 (2012).

Thus, in some situations it may be more desirable to use PS devices which monitor internal organs or tissues rather than superficial skeletal muscle. For example, NIRS devices have sometimes been attached to the surface of a patient's forehead or scalp to monitor cerebrovascular function. Such devices have proven useful in monitoring cerebrovascular functioning in patients during assisted ventilation and during/after cardiopulmonary resuscitation (CPR). See, Frisch, A., et al.; *Potential Utility of Near-Infrared Spectroscopy in Out-of-Hospital Cardiac Arrest: An Illustrative Case Series;* Prehospital Emergency Care, Vol. 16, No. 4: Pages 564-570 (2012); Booth E. A., et al.; *Near-infrared Spectroscopy Monitoring of Cerebral Oxygen During Assisted Ventilation.* Surgical Neurology International; No. 2, Page 65 (2011) and Mullner, M., et al., *Near Infrared Spectroscopy During And After Cardiac Arrest-Preliminary Results;* Clinical Intensive Care, Vol. 6, No. 3, Pages 107-11 (1995). However, the light emitted from PS devices positioned on the surface of the scalp or forehead may be incapable of penetrating to deep brain tissues because before reaching the brain the light emitted from the device must first pass through the patient's skin, skull bone and meningeal tissues.

The prior art has included some PS devices that can be implanted subcutaneously, thereby avoiding light refraction or damping effects of the skin. For example, investigators have reported use of a subcutaneously implanted NIRS device in combination with an Implanted Cardioverter Defibrillator (ICD). In this study, NIRS oximetric measurements were used, in combination with electrical monitoring by the ICD, to distinguish between the onset of a ventricular arrhythmia requiring defibrillation and mere electromagnetic interference or artifacts resulting from erroneous double counting of the electrocardiographic T-wave as an R-wave, ICD lead failure, or other electrocardiographic aberrancies. Bhunia, S. K. et al., Implanted Near-Infrared Spectroscopy For Cardiac Monitoring; Proc. SPIE 7896, Optical Tomography and Spectroscopy of Tissue IX, 789632 (2011). [http://proceedings.spiedigitallibrary.org/proceeding.aspx?articleid=733147]

Also, the prior art has included a number of NIRS devices that are positionable at various locations on the patient's skin, subcutaneously below the skin or within certain anatomical passageways or lumens, to measure physiological properties or concentrations of analytes (e.g., pH, temperature, oxygen tension, oxygen saturation, partial pressure of oxygen, partial pressure of carbon dioxide, hemoglobin concentration, water concentration, hematocrit, glucose concentration, presence of biomarkers, etc.) in underlying organs or tissues. Some but not necessarily all examples of such devices are described in U.S. Pat. No. 5,931,779 (Arakaki, et al.); U.S. Pat. No. 6,212,424 (Robinson); U.S. Pat. No. 6,990,364 (Ruchti et al.); U.S. Pat. No. 7,245,373 (Soller, et al.); U.S. Pat. No. 7,613,489 (Myers); U.S. Pat. No. 7,647,092 (Motz et al.); U.S. Pat. No. 8,277,385 (Berka et al.); U.S. Pat. No. 8,346,329 (Xu et al.); U.S. Pat. No. 8,406,838 (Kato) and U.S. Pat. No. 8,649,849 (Liu et al.) as well as United States Patent Application Publication Nos. 2014/0135647 (Wolf II); 2014/0024904 (Takinami); 2013/0225955 (Schenkman, et al.) and 2011/0184683 (Soller et al.) as well as in U.S. Provisional Patent Application No. 62/072,096 entitled Transesophageal Or Transtracheal Cardiac Monitoring By Optical Spectroscopy filed Oct. 29, 2014, the entire disclosure of each such patent and patent application being expressly incorporated herein by reference. Also, examples of such devices are currently marketed as CareGuide™ Oximeters (Reflectance Medical, Inc., Westborough, Mass.); INVOS™ Somatic/Cerebral Oximetry Monitors (Covidien Respiratory and Monitoring Solutions, Boulder, Colo.); Reveal LINQ™ Insertable Cardiac Monitoring Systems (Medtronic Corporation, Minneapolis, Minn.); FORE-SIGHT ELITE® Cerebral Oxygen Monitors (CAS Medical Systems, Inc., Branford, Conn.) and EQUANOX™ Cerebral/Somatic Tissue Oximetry Devices (Nonin Medical, Inc., Plymouth, Minn.). Some if not all of these NIRS devices utilize specialized apparatus and/or signal processing techniques (e.g, "background subtraction") to minimize or eliminate spectral effects from skin, bone or other intervening tissue that resides between the location of the NIRS device and the organ or tissue of interest.

PS measurements from critical organ tissues (e.g., brain, heart, etc.) could be of greater value than peripheral measurements in many clinical situations, including resuscitation and acute care settings. However, as noted above, transcutaneous devices positioned on the surface of the skin may not be useable to accurately measure physiological variables from certain internal locations because of limitations on the depth of penetration of the light and the need for complex signal processing to subtract or negate the optical effects of whatever light absorbing or refractive matter is located between the light emitter and the target location (referred to generally herein as "intervening matter"). Depending on where the internal location of interest is, such intervening matter may include, for example, skin, fascia, nerves, vessels, muscles, cartilage, bones, connective tissue and body fluids.

Also, PS devices affixed to the surface of a patient's skin may have little or no capability for movement or scanning of tissue. It is desirable for PS devices to be capable of operating at varied wavelengths and/or scanning multiple locations or areas of tissue as such capabilities could be useable for measuring metabolic activity throughout the parenchyma of a particular organ and/or for functional mapping of organs or tissues of interest.

There exists a need in the art for the development of new PS devices and methods capable of overcoming some or all of the above-described shortcomings.

SUMMARY OF THE INVENTIONS

The present invention generally provides devices and methods wherein an optical spectroscopy device is inserted or implanted at an intraosseous, subosseous, epidural, subdural, intraventricular, intramuscular, sub-adipose or other subcutaneous location within the body of a human or animal subject and used for PS monitoring of particular internal target location(s) within the subject's body (e.g., an internal tissue, body fluid, brain, heart, other organ, tumor, etc,).

In accordance with the present invention, there is provided a method for measuring a physiological variable from an internal target location within the body of a subject, such method comprising the steps of: (a) placing an optical spectroscopic device at an intraosseous, subosseous, epidural, subdural, intraventricular, intramuscular, sub-adipose or other subcutaneous location, such optical spectroscopic device comprising an emitter which emits light at one or more wavelengths between approximately 250 nm and approximately 2500 nm and at intensity capable of penetrating from the operating position to the target location and a detector for detecting light that has been emitted from the emitter after said light has undergone dispersion and/or reflection by tissue or body fluid and (b) using the optical spectroscopy device to measure the physiological variable at the internal target location.

Further in accordance with the present invention, there are provided methods and devices of the foregoing character wherein the emitter and/or detector are moveable such so as to scan an area of tissue or obtain measurements of the physiological variable from a plurality of target internal locations. This provides for mapping the measured physiological variable(s) at numerous locations within a tissue or body fluid area of interest or for determining some comparative, blended or computed value (e.g, the average value, highest value, lowest value, etc.) based on a plurality of measurements of the physiological variable(s) throughout a tissue/body fluid area of interest.

Still further in accordance with the present invention, the measured physiological variable(s) may include any variable capable of being measured by the particular wavelength and type of optical spectroscopy being used. For example, in some embodiments the variable(s) may be selected from: pH, temperature, oxygen tension, oxygen saturation, partial pressure of oxygen, partial pressure of carbon dioxide, hemoglobin concentration, water concentration, hematocrit, glucose concentration, the presence/absence of a biomarker, anaylte or other substance, the concentration of a biomarker, anaylte or other substance, and/or the flow rate of blood or other fluid based on changes in concentration of an injected, optically-determinable substance such as indocyanine green or other optical dye.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

DETAILED DESCRIPTION OF THE INVENTION

The following detailed description and the accompanying drawings to which it refers are intended to describe some, but not necessarily all, examples or embodiments of the invention. The described embodiments are to be considered in all respects as illustrative and not restrictive. The contents of this detailed description and the accompanying drawings do not limit the scope of the invention in any way.

Figure 1:
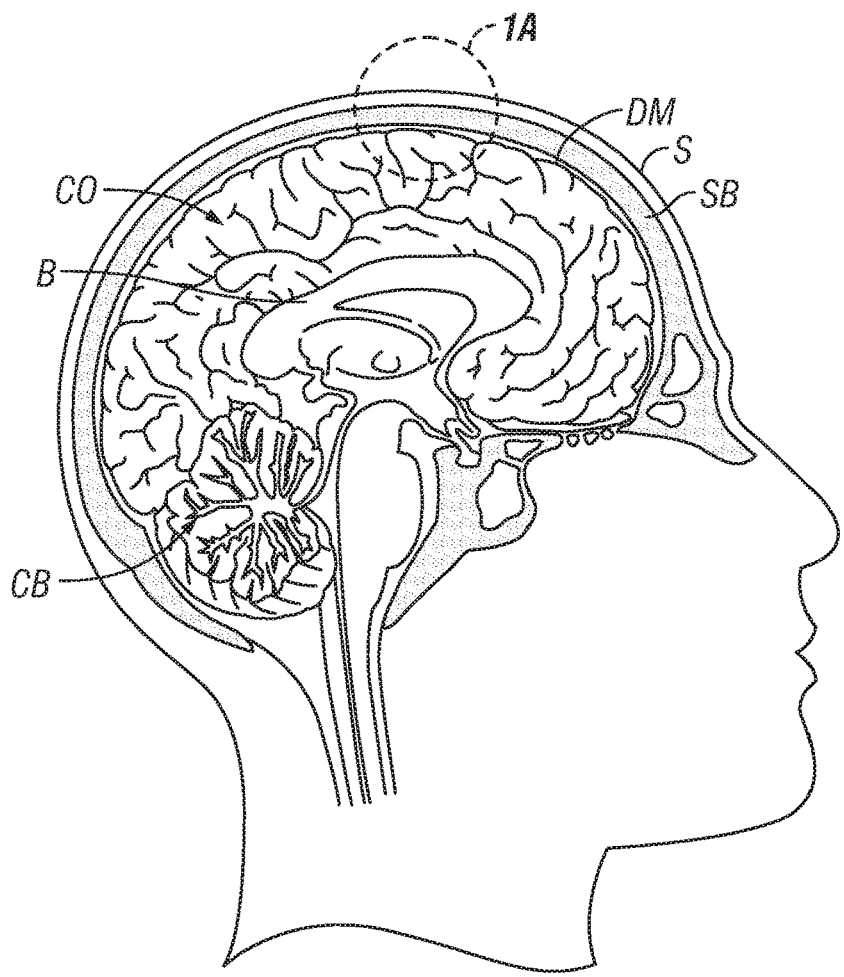
FIG. 1 is a sagittal sectional view of a human head.
Figure 1A:
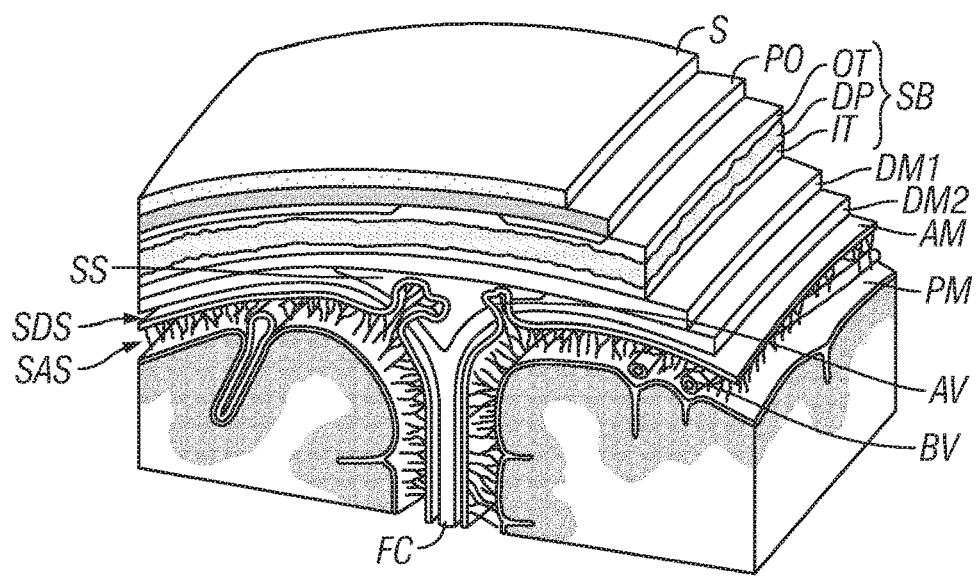
FIG. 1A is an enlarged, cut-away view of area 1A of FIG. 1.

FIGS. 1 and 1A show portions of the brain and cranial anatomy, with specific anatomical structures being identified as follows:

| | |
|---|---|
| B | Brain |
| CO | Cortex |
| CB | Cerebellum |
| DM | Dura Mater |
| DM1 | Periosteal Dura Mater |
| DM2 | Meningeal Dura Mater |
| PM | Pia Mater |
| S | Skin |
| P | Periostium |
| SB | Skull Bone |
| OT | Outer Table |
| DP | Diploe |
| IT | Inner Table |
| SS | Superior Sagittal Sinus |
| EDS | Epidural Space |
| SDS | Subdural Space |
| SAS | Subarachnoid Space |
| AV | Arachnoid Villi |
| BV | Blood Vessels |

Reference to some of all of these anatomical structures is made in the description of examples set forth below. In considering the examples described below, it should be appreciated that the devices and methods of the present invention are useable to obtain oximetric and other measurements from internal locations (e.g., deep brain tissue, heart, other organs, tumors, etc.).

Figure 2:
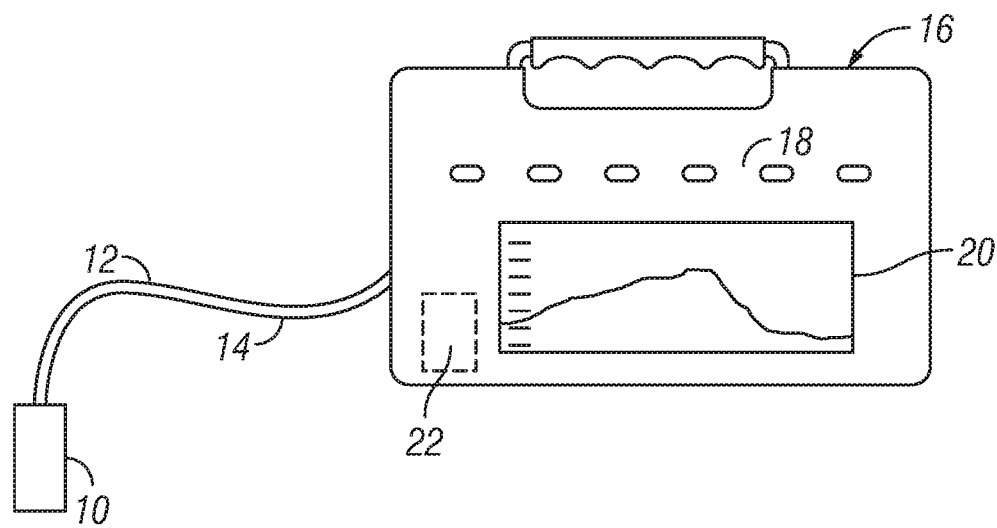
FIG. 2 is a schematic diagram of one example of a system for subcutaneous or intraosseous optical spectroscopy in accordance with the present invention.
Figure 3:
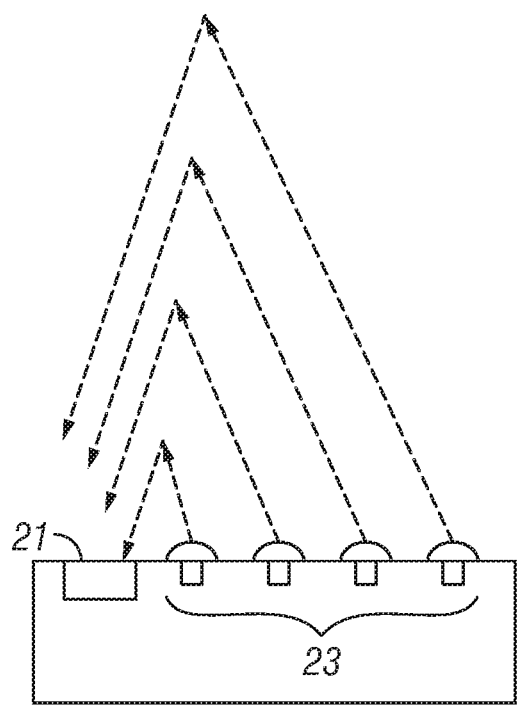
FIG. 3 is a schematic diagram showing an example of an emitter/detector apparatus that may be mounted on or in a device that is insertable to or implantable at a subcutaneous, intraosseous or subosseous location.

FIG. 2 shows an example of a PS device 10 of the present invention connected to a processor/display device 16. The PS device 10 has at least one light emitter and at least one detector. One non-limiting example of an emitter/detector assembly that may be present on the distal end of the PS device 10 is seen in FIG. 3. In the example of FIG. 3, a plurality of LED emitters 23 deliver light at desired wavelength(s) into tissue or body fluid and a detector 21 then receives reflected light after it has passed through and been absorbed/refracted by the tissue or body fluid. This PS device 10 is connected to the processor/display device 16 by way of an emitter lead 12 and a detector lead 14. The processor/display device 16 includes a processing device or controller 22, which may be a microprocessor, chip(s) or other suitable data processing apparatus. Also, in this example, the processor/display device 16 includes a display 20 which displays the physiological variable(s) being measured in numerical, graphic or other suitable form. The processor/display device 16 may also include user interface apparatus 18 whereby a user may input commands, such as commands to turn the system on or off, wavelength selection(s), light intensity selection(s), scanning movement or scanning pattern selections, selection of computations to be performed and display modes or formats to be utilized, etc.

In typical operation, the PS device 10 is inserted or implanted at a desired intraosseous, subosseous, epidural, subdural, intraventricular, intramuscular, sub-adipose or other subcutaneous location within the body of a human or animal subject such that the emitters 23 will cast light toward the internal target location at which it is desired to measure the physiological variable(s). Using the interface 18, the user turns the system on and, in some embodiments may additionally input other parameters or selections as discussed above. The controller 22 then issues control signals, via the emitter lead 12, to cause the emitters 23 to emit the desired light. The detector 21 in turn sends back to the controller 22, via detector lead 14, signals indicative of the refracted light that the detector 21 has received. The controller 22 then processes the signals received from the detector 21 to determine the physiological variable(s) being measured and displays indicia of the measured physiological variable(s) on the display 20.

These devices, including the controller 22, may be constructed, programmed and operated in any suitable way including, for example, in any of the ways described in U.S. Pat. No. 5,931,779 (Arakaki, et al.); U.S. Pat. No. 6,212,424 (Robinson); U.S. Pat. No. 6,990,364 (Ruchti et al.); U.S. Pat. No. 7,245,373 (Soller, et al.); U.S. Pat. No. 7,613,489 (Myers); U.S. Pat. No. 7,647,092 (Motz et al.); U.S. Pat. No. 8,277,385 (Berka et al.); U.S. Pat. No. 8,346,329 (Xu et al.); U.S. Pat. No. 8,406,838 (Kato) and U.S. Pat. No. 8,649,849 (Liu et al.) as well as United States Patent Application Publication Nos. 2014/0135647 (Wolf II); 2014/0024904 (Takinami); 2013/0225955 (Schenkman, et al.) and 2011/0184683 (Soller et al.), the entire disclosures of which are expressly incorporated herein by reference. More specifically, in at least some embodiments of the invention, the processor or controller 22 may receive spectral information from the detector 21 which it then compares to a set (e.g., a library) of stored reference spectra. Those reference spectra may have been predetermined from previously compiled clinical or experimental data or from data determined from a model of light attenuation in the selected target tissue or body fluid. The processor or controller 22 may then identify a member of the set of reference spectra that corresponds to the measured spectral information. The processor may then apply a set of correction factors to correct for intervening matter or other items that distort or interfere with the spectral information and then uses the corrected identified member of the set of spectra as input to a calibration equation to determine a value associated with the particular physiological variable being measured. However, because the present invention provides for positioning the PS device 10 below subcutaneous fat layers, or at an intraosseous, subosseous, epidural, subdural, intramuscular or other subcutaneous location, the amount of intervening matter will typically be less than would be present if the PS device 10 were to be positioned on the surface of the skin.

Figure 4:
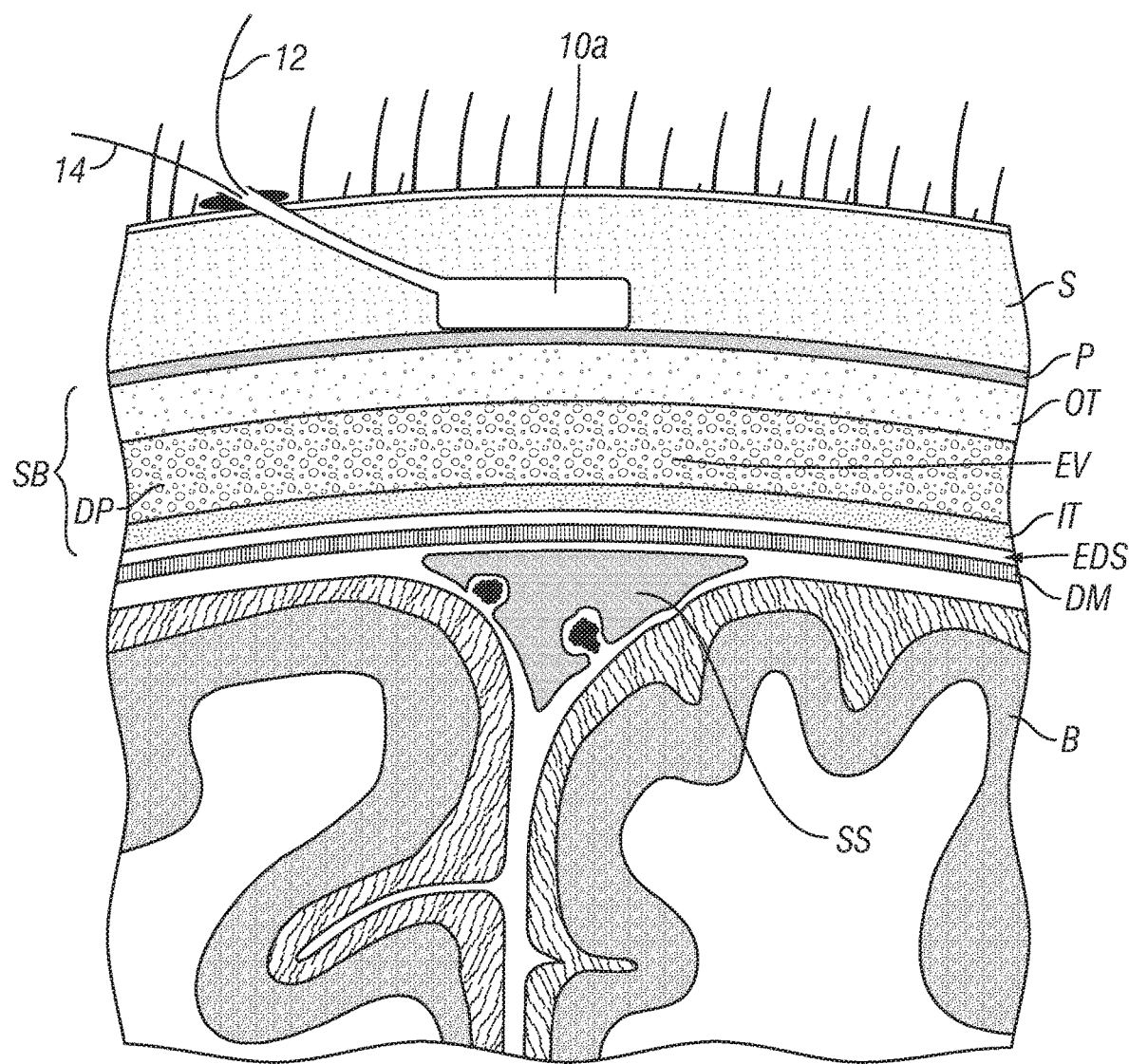
FIG. 4 is a sagittal sectional view of a portion of a human head wherein a PM device has been positioned at a subcutaneous location and is being used for monitoring of physiological variable(s) in the brain in accordance with the present invention.

FIG. 4 shows an example of an embodiment of a PS device 10a of the present invention that has been introduced through a small opening in the skin S (e.g., a small incision or puncture tract) to a subcutaneous position that is below the full thickness of the skin S but immediately above the periostium P which covers the outer surface of the skull bone SB. If it is intended to monitor physiological variable(s) in the subject's brain B using the positioning of the device 10a shown in this example, the light emitted from the PS device 10a need not penetrate through the skin S due to the subcutaneous positioning of the device 10a. However, it would be necessary for the interrogating and refracted light to penetrate through substantial intervening matter, including the periostium P, all layers of the skull bone SB and the meningeal membranes, in order to reach brain B tissue. Thus, when the device 10a is positioned as shown in FIG. 4, it will generally be necessary for the associated processor or controller 22 to be programmed to subtract, negate or otherwise control out the optical effects of all such intervening matter in order to arrive at an accurate determination of the intended physiological variable in tissue of the brain B.

Figure 5:
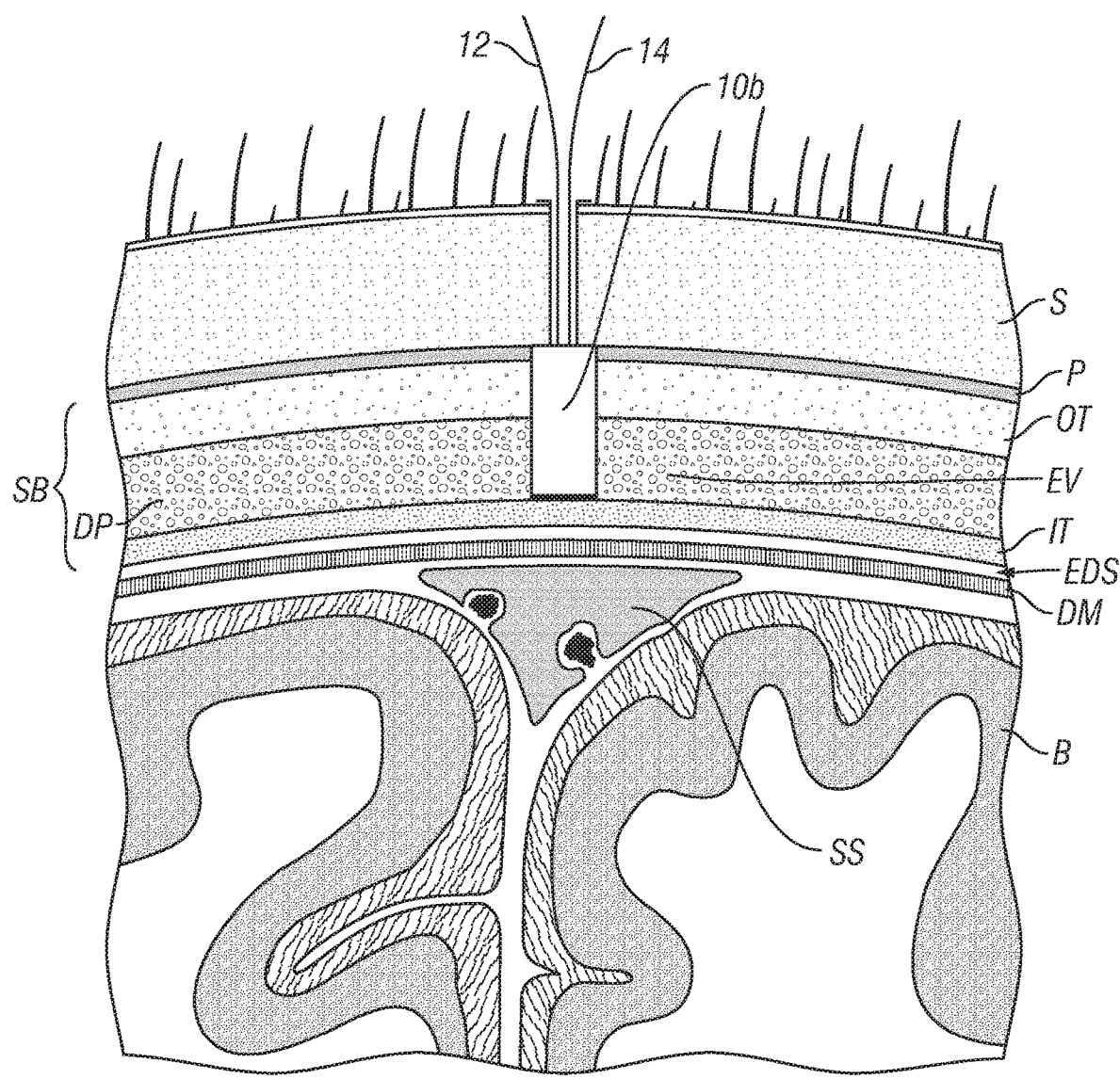
FIG. 5 is a sagittal sectional view of a portion of a human head wherein a PM device has been positioned at an intraosseous location and is being used for monitoring of physiological variable(s) in the brain in accordance with the present invention.

FIG. 5 shows another embodiment of a PS device 10b of the present invention that has been introduced through a small opening in the skin S (e.g., a small incision or puncture tract) and through a partial-thickness notch or bored area in the skull bone SB such that the device 10b is at an intraosseous location within the skull bone SB. The notched or bored area is created by removing an area of the outer table OT of the skull bone SB. Optionally, some or all of the underlying region of diploe DP may also be removed, leaving the inner table IT of the skull bone SB substantially intact as shown in FIG. 5. This type of partial-thickness notch or bored area in the skull bone SB may be created by any suitable means, including but not limited to techniques and devices known for harvesting partial thickness bone grafts as described in; Strong, E. B. et al.; *Calvarial Bone Graft Harvest: A New Technique; Otolaryngology—Head and Neck Surgery, Vol. 143*, Issue 6, Pgs. A1-A18, 737-854 (December 2010) and Yoshimura, Y., et al. *An Instrument for Harvesting the Outer Table of the Skull*; Journal of Craniomaxillofacial Surgery, Vol. 18, No. 4, Pgs. 179-81 (May 1990). After the partial thickness notch or bore has been formed in the skull bone SB, the optical spectroscopy device 10b is positioned within the skull bone SB as shown in FIG. 5 so that light from the emitters 23 will pass through the inner table IT of the skull bone SB, through the meningeal tissues and into the brain B. This intraosseous positioning of the device 10b may allow the interrogating light to penetrate to deeper locations in the brain B than would be possible if the device 10B were positioned outside the full-thickness skull bone SB in the manner shown in FIG. 4 or on the outer surface of the skin as in the prior art. Also, in addition to improving the potential depth of penetration, the intraosseous positioning of the device 10b seen in FIG. 5 eliminates the presence of the periostium P, outer table OT and, optionally, all of part of the diploe DP as intervening matter thereby lessening the complexity of corrective computation required for the processor or controller 22 to fully negate or control out the optical effects caused by intervening matter.

While the example of FIG. 5 specifically shows the device positioned at an intraosseous position in skull bone SB for monitoring the brain B, it is to be appreciated that the same type of intraosseous positioning may be accomplished in other bones of the body. For example, the human sternum is a flat bone of the thorax that overlies the heart. An opening in the skin may be created over a desored location on the sternum and the above-described techniques (or other techniques) may be used to create a partial thickness bore or notch into the anterior surface of the sternum so that the device 10b can be inserted to an intraosseous operating position within the sternum for monitoring physiological variable(s) in the heart or thoracic blood vessels. Specifically, the manubrium and sternum body are two relatively wide areas of the sternum which consist of anterior and posterior layers of dense compact bone with less dense, spongy, cancellous bone in between. An area of the anterior compact bone may be bored through or removed and, optionally, some amount of the underlying cancellous bone may also be removed, leaving the posterior layer of compact bone intact. The device 10b would then the inserted into this partial-thickness notch or cavity so that it need only cast light through the intact posterior layer of compact bone (and any remaining amount of cancellous bone) rather than having to cast light through the full thickness of the sternum.

In some cases, the spectral properties of the CSF may be monitored by placing the tip of the trocar into the EDS. The spectral properties of the CSF can then be monitored to detect such things as hematocrit to detect bleeds.

Figure 6:
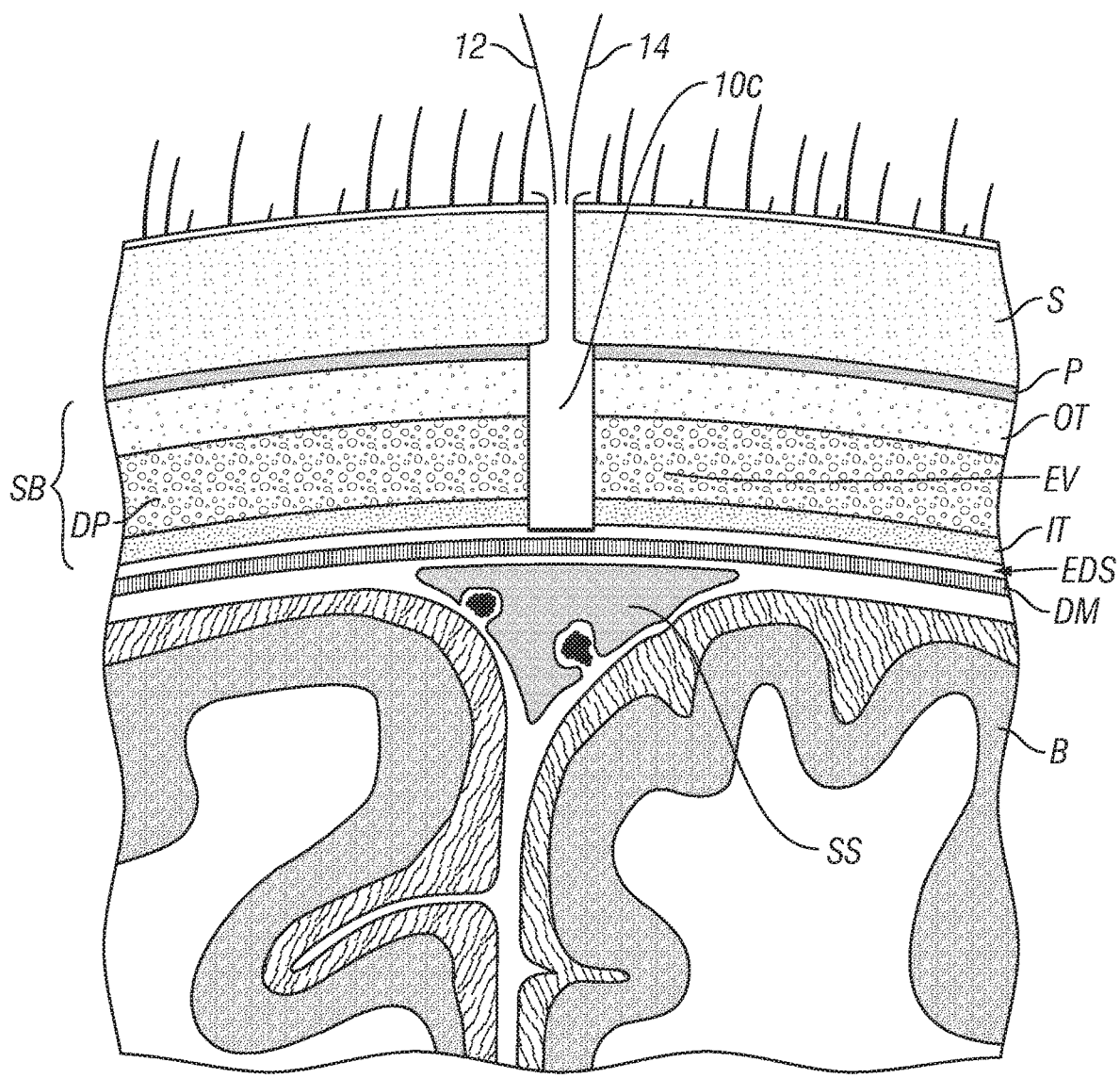
FIG. 6 is a sagittal sectional view of a portion of a human head wherein a PM device has been positioned at a subosseous location and is being used for monitoring of physiological variable(s) in the brain in accordance with the present invention.

FIG. 6 shows another embodiment of the PS device 10c introduced through a small opening in the skin S (e.g., a small incision or puncture tract) and through a full-thickness opening in the skull bone SB such that the device 10c is at a subosseous location (i.e. below the level of the skull bone SB adjacent to the full-thickness opening but directly aligned with the full-thickness opening in the skull bone SB. As shown, no skull bone SB directly overlies the device 10c during its operation. In the example shown, the distal end of the device is within the epidural space EDS but it is to be appreciated that in some applications it may be desirable to advance the device 10c into or through the dura mater DM and/or other meningeal tissues or fully into a ventricle of the brain or other location within the brain B itself. The full thickness opening in the skull bone SB may be created through a small incision of puncture tract in the skin S using any suitable device or methodology, such as by way of a burr hole or trephination procedure of the type typically used for insertion of intracranial drainage or pressure monitoring catheters and/or other intracranial devices. After the full thickness opening has been formed in the skull bone SB, the optical spectroscopy device 10c is advanced through the skull bone SB as shown in FIG. 6 so that light from the emitters 23 will pass through any intervening meningeal tissues or fluid and into the tissue of the brain B where the physiological variable(s) is/are to be measured. This subosseous positioning of the device 10c may allow the interrogating light to penetrate to even deeper locations in the brain B than would be possible if the device 10c were positioned outside of or within the skull bone SB as described above with respect to FIGS. 4 and 5 or on the outer surface of the skin as in the prior art. Also, in addition to improving the potential depth of penetration, the subosseous positioning of the device 10c seen in FIG. 6 eliminates the presence of the any skull bone SB as intervening matter thereby further lessening the complexity of corrective computation required for the processor or controller 22 to fully negate or control out the optical effects caused by intervening matter.

Although the example of FIG. 6 specifically shows the device 10c positioned at a subosseous position below the skull bone SB for monitoring the brain B, it is to be appreciated that the same type of subosseous positioning may be accomplished in other bones of the body. For example, an opening in the skin may be created over the maubrium or bodu of the sternum as described above and a full thickness opening may be drilled or otherwise formed in the sternum. The device 10c could then be inserted through the opening in the sternum to a position that is adjacent to the outer surface of the pericardium. When so positioned, the device 10c may be used for direct monitoring physiological variable(s) in the heart or thoracic blood vessels.

Figure 7:
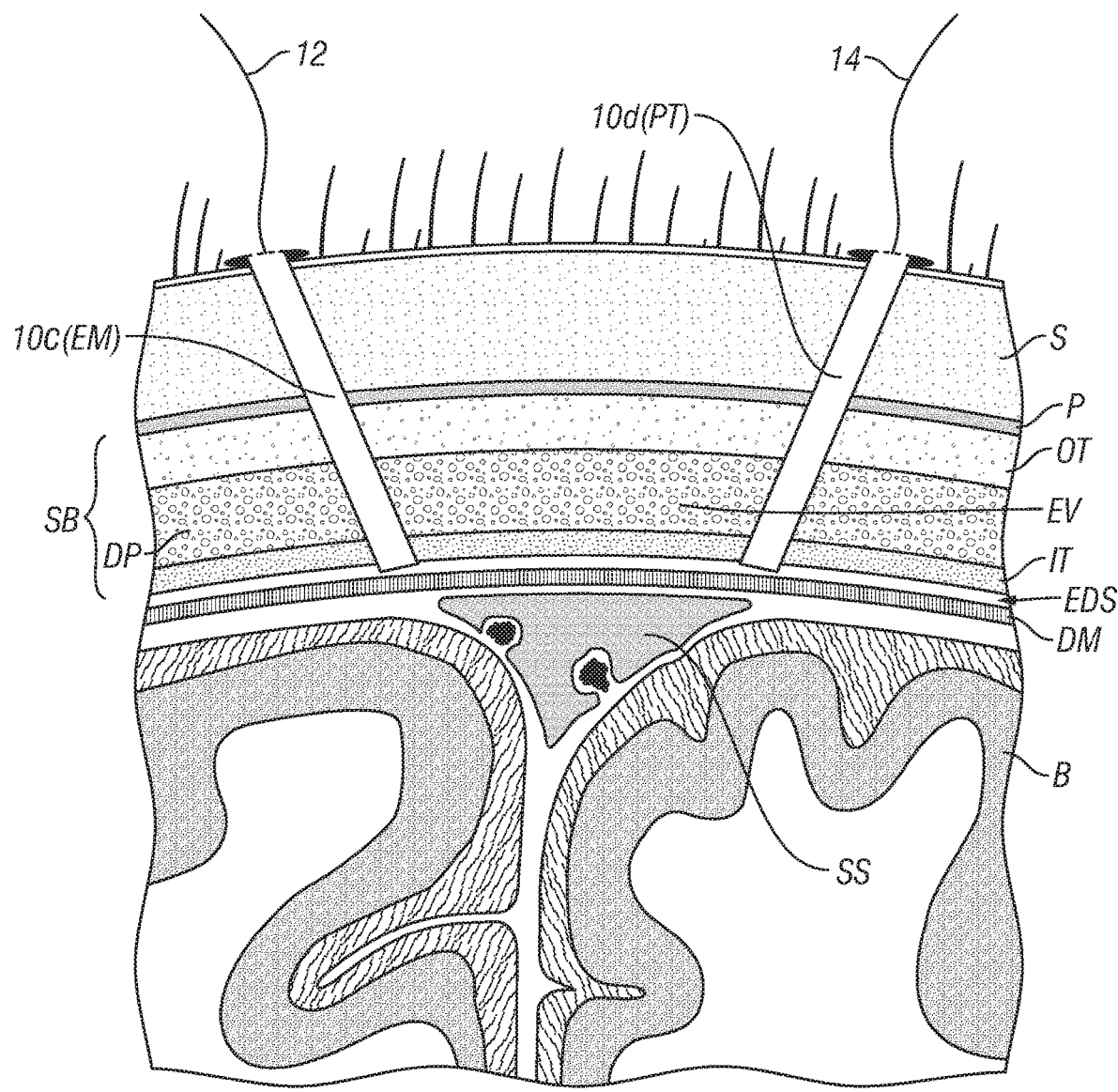
FIG. 7 is a sagittal sectional view of a portion of a human head wherein separate emitter and detector apparatus have been positioned at separate subosseous locations and are being used for monitoring of physiological variable(s) in the brain in accordance with the present invention.

It is to be appreciated that the optical spectroscopy devices 10 of the present invention need not be formed as one-piece devices in the manner shown in FIGS. 1-6. Rather, in some embodiments, these devices may comprise two or more separate or interconnected components. For example, FIG. 7 shows an example of an optical spectroscopy device 10d wherein the emitter(s) is/are housed in one elongate member component 10d(em) and the detector(s) is/are housed in another elongate member component 10d(dt). These components 10d(em) and 10d(dt) are separately positionable at desired locations to perform the intended physiological monitoring. In the non-limiting example of FIG. 7, the separate components 10d(em) and 10d(dt) are inserted through separate scalp incisions and separate full thickness burr holes to subosseous locations whereby their distal ends (where the emitter(s) and detector(s) are located) are within the epidural space EDS. Also in this example, the components 10d(em) and 10d(dt) are angled inwardly toward one another to facilitate penetration of the light to the desired area of the brain and optimal receipt of the refracted incident light by the detector(s). It is to be appreciated that such angling of the components 10d(em) and 10d(dt) is optional and may not be necessary or desirable in all applications.

Figure 8:
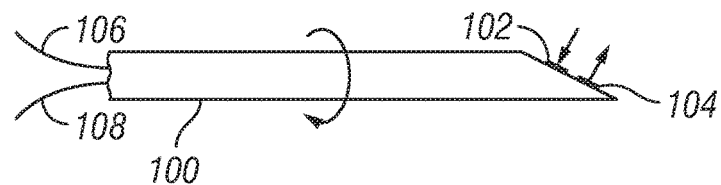
FIG. 8 is a diagram of a distal portion of a rotatable PM device of the present invention useable for measuring physiological variable(s) from multiple target locations and/or for scanning an area within a subject's body.
Figure 8A:
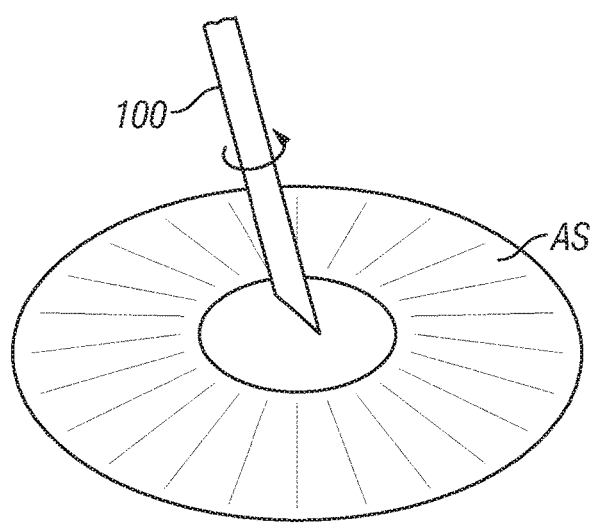
FIG. 8A is a schematic diagram of the device of FIG. 8 being used to scan an annular area within a subject's body.

FIG. 8 shows another embodiment of an optical spectroscopy device 100 which comprises an elongate member which has emitter(s) 104 and detector(s) 102 mounted on an angled or beveled distal end of the device 100, as shown. In this manner, the emitter(s) 104 and detector(s) 102 are aimed at an angle relative to the longitudinal axis of the device 100. The distal tip of this device 100 may be blunt and atraumatic or pointed and tissue-penetrating, depending on the intended application and means used for insertion of the device 100 to the intended operative location within the subject's body. After the device has been inserted to an intended intraosseous, subosseous, epidural, subdural, intraventricular, intramuscular, sub-adipose or other subcutaneous locations, the emitter(s) 104 and detector(s) 102 will communicate via emitter lead 108 and detector lead 106 to a processor/display device 16 in the same manner as described above and the device 100 may thus be used in the above-described manner to determine physiological variable(s) in at desired internal target locations within a subject's body. However, because of the angular aiming of the emitter(s) 104 and detector(s) 102 in this device 100, physiological variable(s) may be measured in an area surrounding the device 100 by rotating the device 100, as depicted in FIG. 8A. In this manner, the device 100 may be used to scan or map an area (e.g. an annular) area that surrounds the device 100. Also, the device 100 may be longitudinally advanced and/or retracted in addition to being rotated, thereby scanning, mapping or obtaining measurements from a three dimensional cylindrical region which surrounds the longitudinal path of the device 100.

Any of the devices 10, 100 of the present invention may be integrated or combined with other devices, such as catheters, scopes or cannulae, which are inserted into a subject's body. For example, the device 100 shown in FIGS. 8 and 8a may be integrated with an intracranial drainage and/or pressure monitoring catheter of a type commonly inserted into a ventricle of the brain for monitoring intracranial pressure and/or for sampling/venting cerebrospinal fluid. In such a device, the emitter(s) 104 and detector(s) 102 can be used to measure physiological variables in the brain while other aspects of the device are used for measuring intracranial pressure, venting or sampling cerebrospinal fluid, etc.

Figure 9:
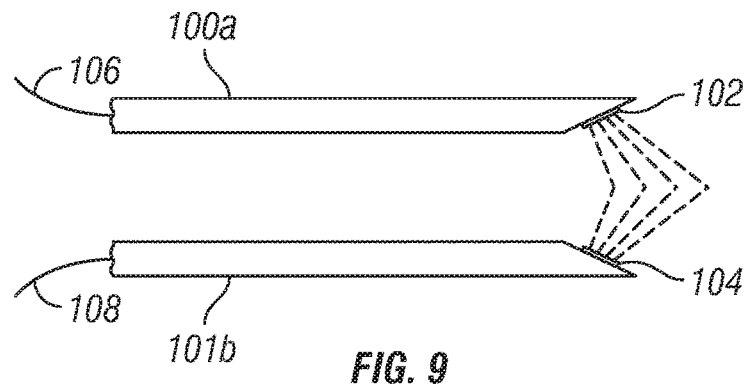
FIG. 9 is a schematic diagram of distal portions of two PM devices useable in combination with each other for measuring physiological variable(s) from multiple target locations and/or for scanning an area within a subject's body.
Figure 9A:
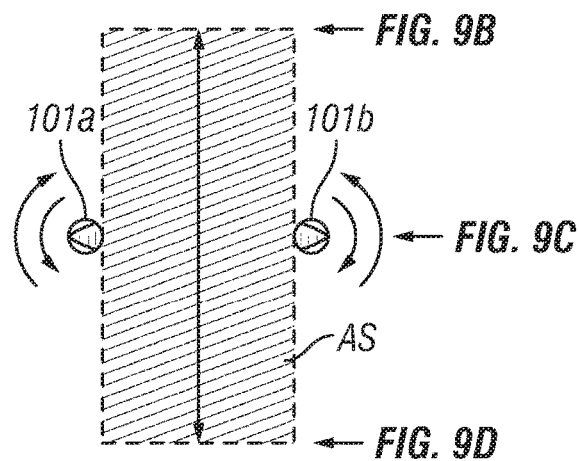
FIG. 9A is a schematic diagram of the devices of FIG. 9 being used in combination with each other to scan a planar area within a subject's body.
Figure 9B:
FIG. 9B is a schematic diagram showing the relative rotational orientations of the PM devices at the location labeled "FIG. 9B" on FIG. 9A.
Figure 9C:
FIG. 9C is a schematic diagram showing the relative rotational orientations of the PM devices at the location labeled "FIG. 9B" on FIG. 9A.
Figure 9D:
FIG. 9D is a schematic diagram showing the relative rotational orientations of the PM devices at the location labeled "FIG. 9B" on FIG. 9A.

In the alternative embodiment shown in FIGS. 9-9D, the device comprises a first elongate member 100a having an angled or beveled distal end upon which detector(s) 102 is/are positioned and a second elongate member 101b having an angled or beveled distal end upon which emitter(s) 104 is/are positioned. In this manner the emitter(s) 104 and detector(s) 102 are aimed at an angles relative to the longitudinal axes of the elongate members 100a and 101b. The distal tips of the elongate members 100a, 101b may be blunt and atraumatic or pointed and tissue-penetrating, depending on the intended application and means used for insertion. In operation, the elongate members 100a, 101b are inserted into the body on opposite sides of a target area of tissue and/or body fluid from which it is desired to measure physiological variable(s). Thereafter, the elongate members 100a, 101b are partially rotated as shown in FIGS. 9A-9D, thereby scanning, mapping or obtaining measurements over a substantially planar area, as indicated in FIG. 9A. Optimally, the elongate members 100a, 101b may be longitudinally advanced or retracted and these rotational scanning may be repeated at different (e.g., incremental) depths of penetration to thereby scan, map or obtain measurements from a three dimensional volume of tissue and/or body fluid.

Figure 10:
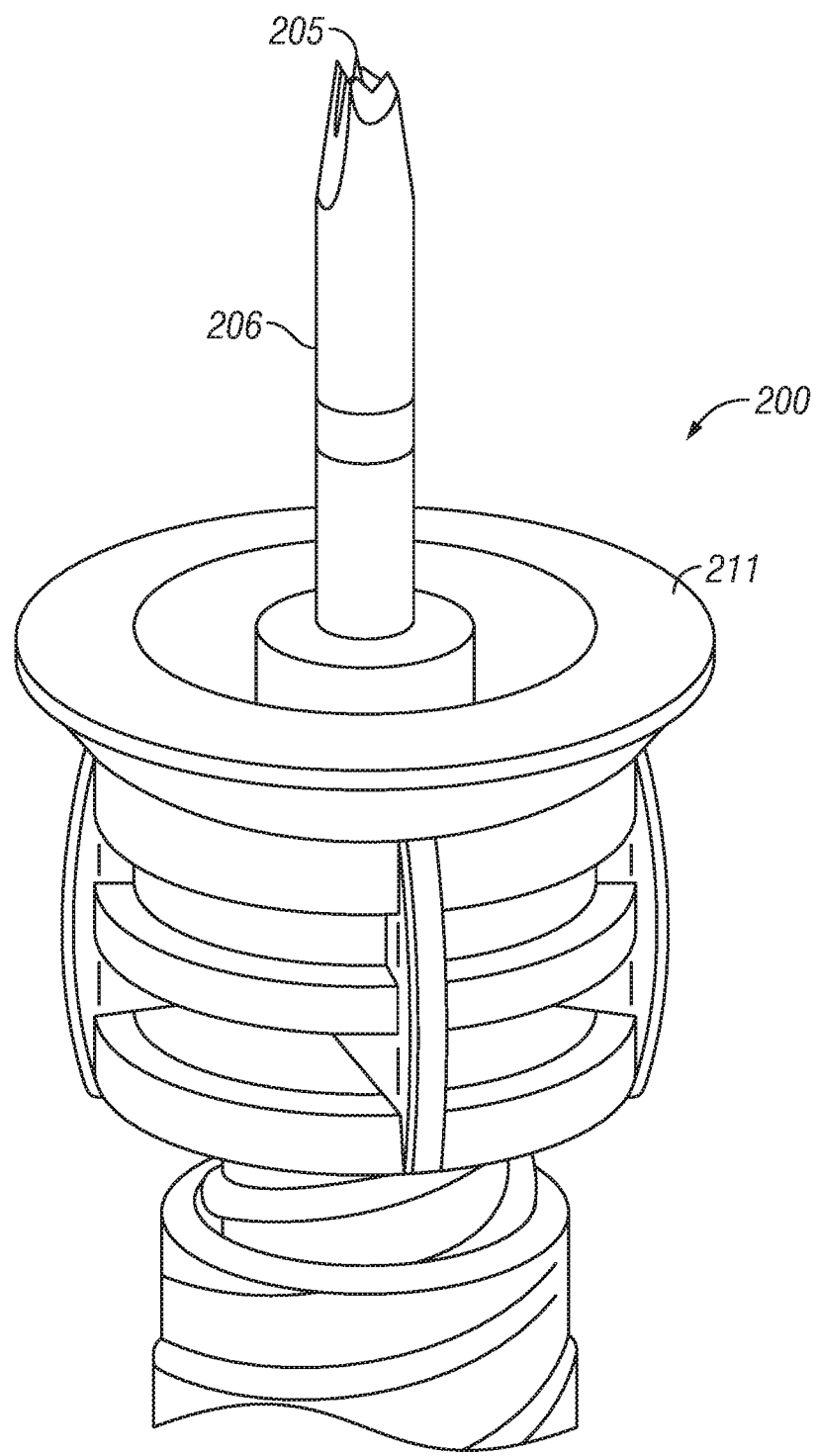
FIG. 10 is partial perspective view of the distal end of a cannula/obturator assembly useable for introducing an optical spectroscopy device to a desired intraosseous or other location.
Figure 10A:
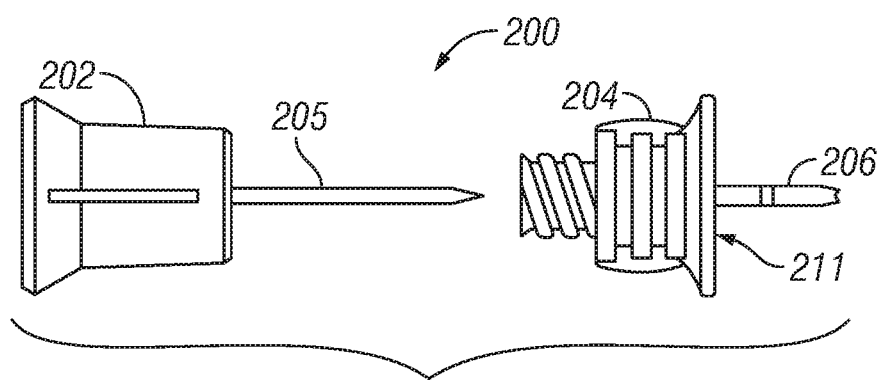
FIG. 10A is an exploded side view of obturator member and cannula member components of the assembly shown in FIG. 10.
Figure 10B:
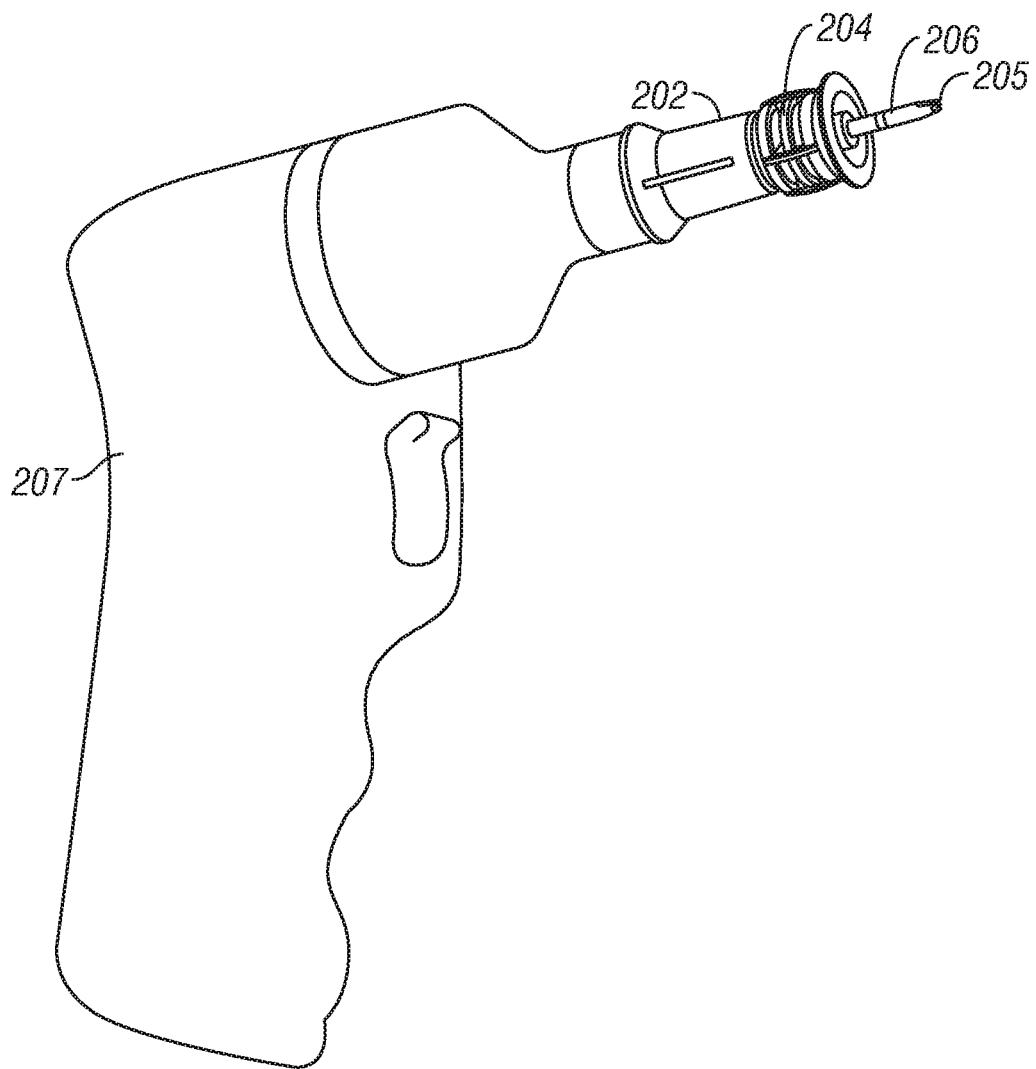
FIG. 10B is a perspective view of the cannula/obturator assembly mounted on a driver device for rotatably driving the cannula obturator assembly into a bone or previously formed pilot bore in a bone.

In at least some embodiments of the invention, the optical spectroscopic device 10, 100 may be inserted into or through an introducer, such as a cannula, trocar, guide, introducer, tube or other device which remains implanted along with the optical spectroscopic device 10, 100 and which may, in some cases, be used for additional functions as well as providing an insertion channel through which the optical spectroscopic device 10, 100 is inserted. One non-limiting example of such a system is an intraosseous cannula system 200 of the type shown in FIGS. 10-10d. Intraosseous cannula systems are typically used for infusion of fluids, medications, blood/blood products, crystalloids, etc. into vascularized bone, such as the sternum or skull, in acute care or trauma resuscitation settings where establishing intravenous access is not possible or not feasible. Many of the patients being treated in such acute care or trauma resuscitation situations could also benefit from intraosseous implantation of a optical spectroscopic device 10 or 100 of the present invention. FIGS. 10 through 10F show one non-limiting example of an intraosseous cannula system 200 that is useable to facilitate intraosseous implantation of a optical spectroscopic device 10d of the present invention alone or in combination with intraosseous infusion of a desired infusate.

The intraosseous trocar system shown in FIGS. 10 through 10F comprises an obturator portion 202 and a cannula portion 204. The obturator portion 202 comprises a hub having one or more elongate obturator member(s) 205 extending distally from the hub. The cannula portion 204 comprises a hub 204 having an elongate cannula 206 with one or more lumen(s) extending distally from the hub. Initially, the obturator member(s) is/are inserted into the lumen(s) of the cannula 206 to facilitate insertion or rotational driving of the obturator/cannula combination into cancellous bone CB which is vascularized. Thereafter, the obturator portion 202 is removed, leaving the cannula portion 204 in place. A device optical spectroscopic device 10d of the present invention may then be introduced into or through a lumen of the cannula 206 and thereafter used for monitoring of desired variables as described in detail above.

In the particular example shown in FIGS. 10 through 10F, the cannula 206 has an optional trocar tip, the obturator has an optional needle tip and the obturator/cannula combination is attachable to a hand held driver 209. The driver 209 is useable to rotatably drive the obturator/cannula into a desired bone (e.g., sternum or skull). In some cases, the cutting surface of the trocar tip on the cannula 206 may be a slightly smaller diameter than the corresponding shaft region of the obturator 204, with additional fluting in the transition region between the cutting zone and the barrel that causes a screwing action that force-fits the needle tip of the obturator 204 into a pilot hole that has been drilled into the bone. An annular abutment surface 211 may be provided to limit the depth of insertion or advancement. The trocar tipped cannula portion 204 may be frictionally held in place by the outward force of its main barrel against the bone. Alternatively or in addition, support materials may be provided for affixing the hub of the cannula portion 204 to the patient's body (e.g., head or chest). The affixation material may be as simple as an adhesive strip or tape or more elaborate, in the form of a flexible, elastic material such as a polymer or fabric that will stretch as a band around the head and cover the trocar insertion point to provide control of the location and orientation of the cannula 204 relative to the bone (e.g., skull or sternum) as well as strain relief of the cables 12, 14 that exit the lumen of the cannula portion 204 during use.

In some versions, the cutting surface of the trocar tip on the cannula 204 may be of equal or larger diameter than the barrel portion. In this case, the driver 207 may incorporate circuitry and apparatus to monitor drilling torque, as well as optionally pressure, so that it will automatically stop rotating via a clutch and brake mechanism as well as retract slightly so as not to drill into any body cavity or organ underlying the bone into which the device is being inserted (e.g., sternum or skull). The retraction can be accomplished via a spring mechanism that loads the drilling shaft or alternatively may be accomplished via a piezoelectric actuator. The pressure sensor may also be incorporated into the piezoelectric actuating mechanism. The pressure sensor can also be based on a piezoelectric, pressure sensing element.

Figure 10C:
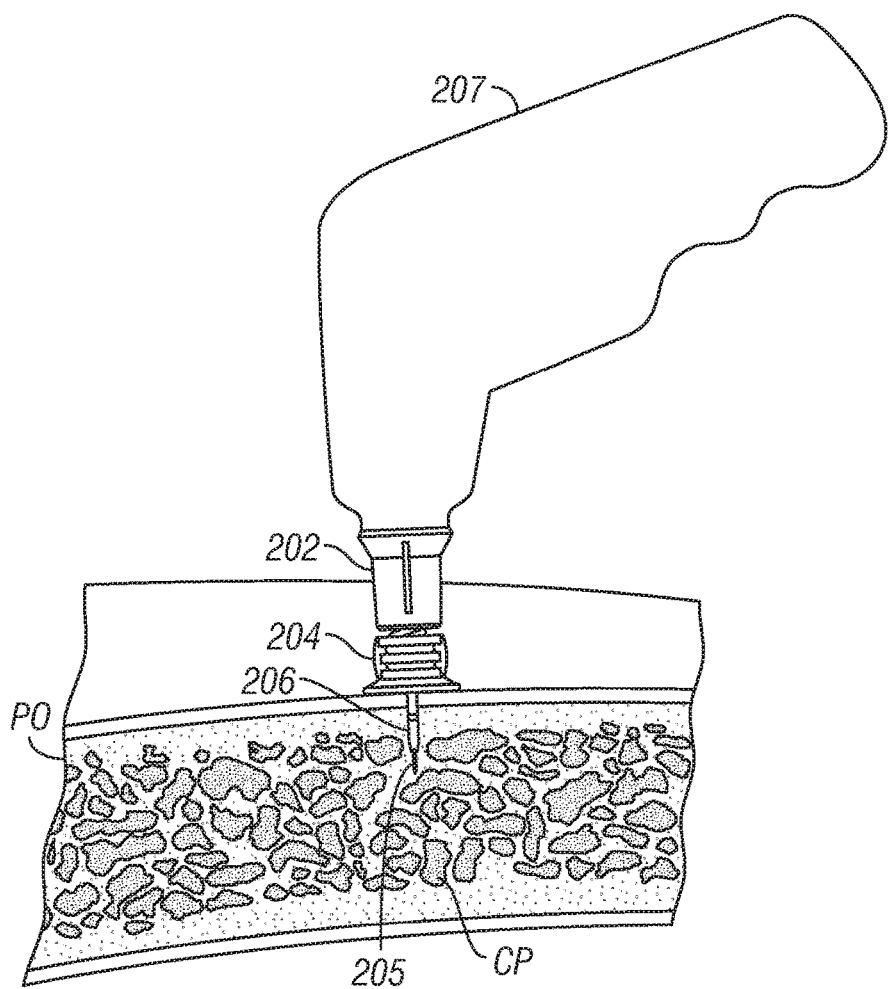
FIGS. 10C through 10F show steps in a method for using a cannula/obturator assembly of the type shown in FIGS. 10-10B for introduction of an optical spectroscopy device to an intraosseous location in bone with or without concomitant or concurrent intraosseous infusion.
Figure 10D:
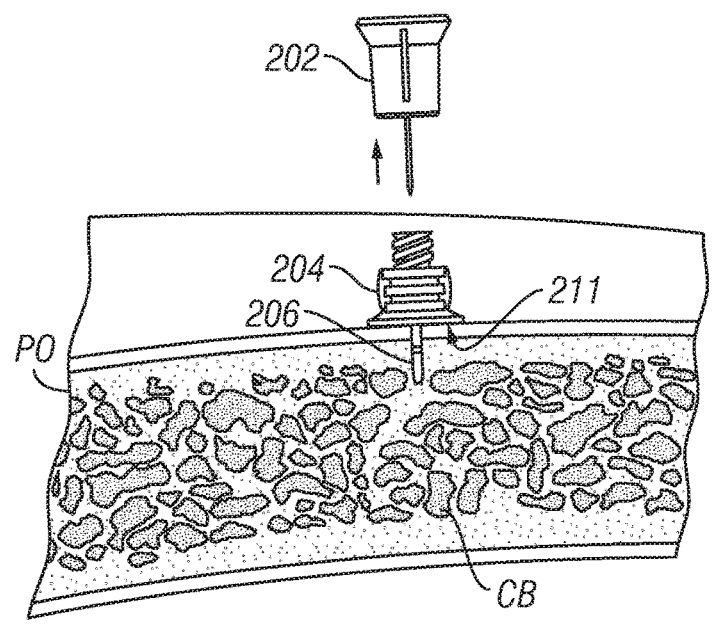
Figure 10E:
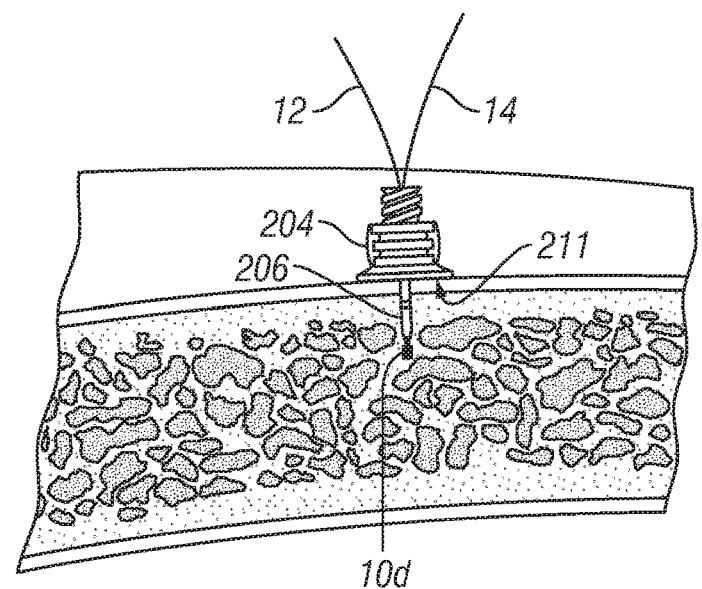
Figure 10F:
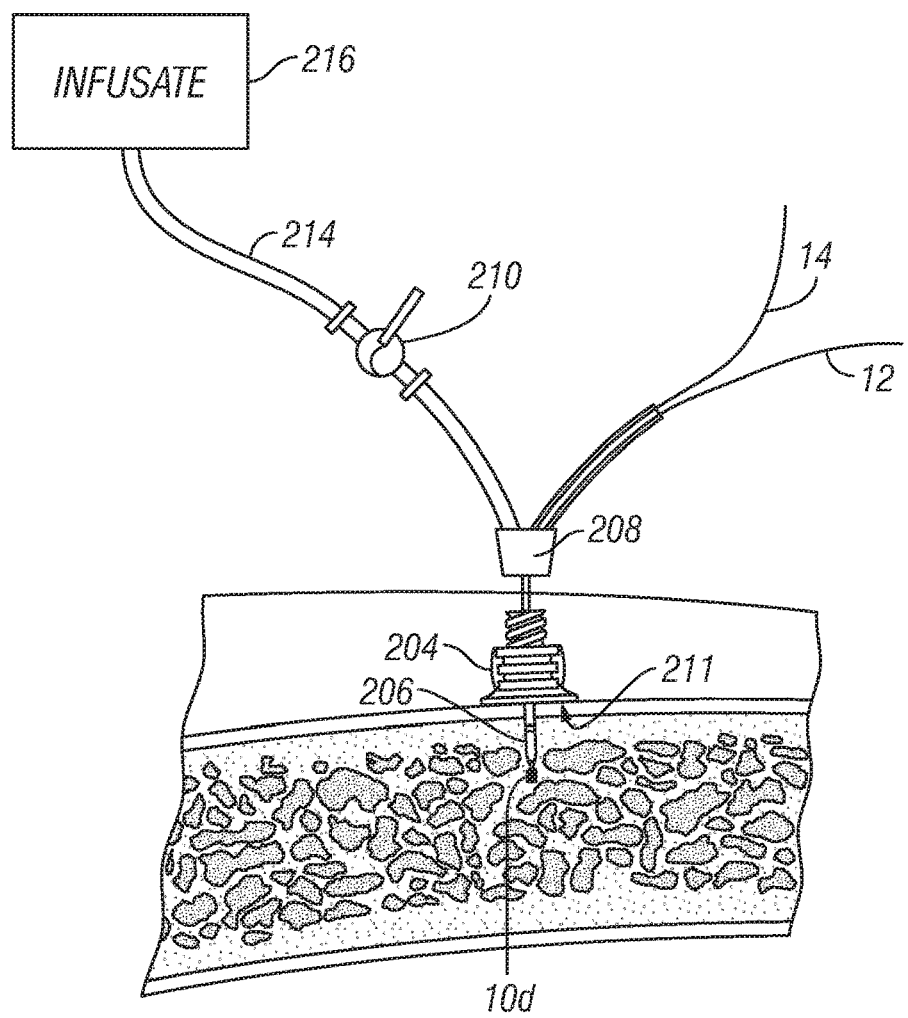

A non-limiting example of this insertion technique is depicted in FIGS. 10C through 10F. In FIG. 10C, the obturator/cannula assembly 202/204 is attached to the driver 208 and the driver 208 is used to drive the obturator/cannula assembly 202/204 through the periostium PO and into the desired bone (e.g., sternum or skull) at a depth where the distal end of the elongate cannula 206 is within cancellous bone CB.

As shown in FIG. 10D, the driver 208 is then detached, the obturator portion 202 is separated from the cannula portion 204 and the obturator portion 202 is removed, leaving only the cannula portion 204 in place.

If it is desired to use the implanted cannula portion 204 only for insertion of the optical spectroscopic device 10d of the present invention, the device 10d of the present invention may simply be inserted through a lumen (typically a single lumen) of the cannula 206 as seen in FIG. 10E.

Alternatively, if it desired to use the implanted cannula portion 204 for both insertion of the optical spectroscopic device 10d of the present invention and infusion of a substance (e.g., fluids, medications, blood/blood products, crystalloids, etc.), the device 10d of the present invention may be inserted through a lumen of the cannula 206 and substance administration apparatus 210, 214, 216 may be connected to that same lumen (if a single lumen cannula) or to a separate lumen (if a dual lumen cannula) to facilitate the desired infusion of substance(s) concurrently or separately with use of the optical spectroscopic device 10d. In the particular example shown, a Y adapter 208 is provided on the proximal end of the cannula portion 204 with the optical spectroscopic device 109 being inserted through one side of the Y adapter 208 and a substance administration tube 214 is connected to the other side of the Y adapter 208. The substance administration tube is connected to a reservoir (e.g., IV bag or bottle) containing the infusate and optionally an infusion control apparatus 210, such as a stopcock or clamp, may be provided on the infusion tube 214. When necessary, the infusion of infusate may be stopped at times when the optical spectroscopic device 10d is being used to obtain measurements thereby avoiding interference or errors due to the concurrently flowing infusate.

In any of the embodiments capable of obtaining pluralities of measurements from areas or three dimensional volumes of tissue or body fluid, the controller 22 of an associated processor/display device 16 may be programmed to perform desired mapping of the measured values over or within the scanned area or volume, or to otherwise perform computations to arrive at desired comparative, blended or computed value (e.g, the average value, highest value, lowest value, etc.) based on a plurality of measurements of the physiological variable(s) throughout a tissue/body fluid area of interest.

In at least some embodiments of the present invention, the emitters 23 may comprise LEDs or other suitable light emitters which emit near-infrared light having a wavelength in the range of from approximately 600 nm to approximately 2500 nm and/or ultraviolet light having a wavelength in the range of from approximately 200 nm to approximately 400 nm.

In some embodiments, the detector(s) 21 or 102 may be capable of measuring the incident photonic intensity at more than one wavelength or ranges of wavelengths. For instance the detector(s) 21 or 102 may comprise spectroscopic benches capable of generating spectrographic curves for analysis, such as is found in the Reflectance NIR system. The detector(s) 21 or 102 may also comprise an optical element that focuses the light incident on it onto an optically conductive pathway (e.g. a fiber optic cable) that runs alongside or inside the device and the actual sensing element of the detector 21 or 102 may be a reusable element that attaches to the device or is located inside the processor/display device 16.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A system for measuring a physiological variable from an internal target location within the body of a subject comprising:
   an optical spectroscopic apparatus operative to measure the physiological variable at the internal target location, configured to be inserted through a full-thickness opening in a bone of the subject and to thereafter operate from an operating location directly aligned with said full-thickness opening, said optical spectroscopic apparatus comprising:
   an emitter configured to emit light at one or more wavelengths between approximately 250 nm and approximately 2500 nm at an intensity capable of penetrating from said operating location to the internal target location;
   a detector for detecting lights that has been emitted from the emitter after said light has undergone dispersion and/or reflection by tissue or body fluid; and
   a processor or processing device configured to:
   a) receive spectral information from the detector,
   b) compare the spectral information to a set of spectra determined from a model for light attenuation to identify a member of the set of spectra that corresponds to the measured spectral information,
   c) correct the identified member of the set of spectra using a set of spectral correction factors that account for intervening matter, and
   d) use the corrected identified member of the set of spectra to determine a value associated with the particular physiological variable being measured.

2. A system according to claim 1 wherein the physiological variable comprises a variable selected from pH, temperature, oxygen tension, oxygen saturation, partial pressure of oxygen, partial pressure of carbon dioxide, hemoglobin concentration, water concentration, hematocrit, glucose concentration, the presence/absence of a biomarker, anaylte or other substance, the concentration of a biomarker, anaylte or other substance, and flow rate of blood or other fluid based on changes in concentration of an injected, optically-determinable substance such as indocyanine green or other optical dye.

3. A system according to claim 1 wherein the emitter emits light selected from near-infrared light and ultraviolet light.

4. A system according to claim 1 wherein the emitter comprises a plurality of emitters which emit light at a plurality of different wavelengths.

5. A system according to claim 1 wherein the emitter comprises at least one light emitting diode.

6. A system according to claim 1 further comprising an apparatus useable to facilitate introduction of the optical spectroscopic apparatus into or through bone to an intraosseous or subosseous operating location.

7. A system according to claim 6 wherein the apparatus useable to facilitate introduction of the optical spectroscopic apparatus into or through bone comprises at least one of: an introducer device that is advanceable into or through bone and apparatus for cutting or boring into or through bone to facilitate introduction of the optical spectroscopic apparatus into or through bone such that the optical spectroscopic apparatus is positioned at an intraosseous or subosseous operating location.

8. A system according to claim 6 wherein the bone is skull bone and wherein the internal target location is in a brain.

9. A system according to claim 8 wherein the apparatus for cutting or boring into bone comprises apparatus which removes an area of the outer table with or without a quantity of underlying diploe while leaving the inner table of the skull bone substantially intact and wherein the optical spectroscopic apparatus is positionable within the area from which the apparatus has removed the outer table or outer table and quantify of underlying diploe so that light from the emitter passes through the inner table of the skull bone.

10. A system according to claim 6 wherein the bone is sternum and wherein internal target location is in a heart or intrathoracic blood vessel.

11. A system according to claim 10 wherein the apparatus for cutting or boring into bone comprises apparatus which removes an area of the anterior layer of compact bone from either the manubrium or body of the sternum, alone or along with a quantity of underlying cancellous bone, leaving the posterior layer of compact bone intact and wherein the optical spectroscopic apparatus is positionable in the area from which the apparatus has removed the anterior layer of compact bone or the anterior layer of compact with a quantity of underlying cancellous bone so that light from the emitter passes through the posterior layer of compact bone.

12. A system according to claim 10 wherein the optical spectroscopic apparatus is positionable at an operating location outside of the pericardium.

13. A system according to claim 6 wherein the bone is skull bone and wherein the optical spectroscopic apparatus is positioned at a subdural location.

14. A system according to claim 6 wherein the bone is skull bone and wherein the optical spectroscopic apparatus is positioned at an intraventricular operating location within the subject's brain.

15. A system according to claim 14 wherein the optical spectroscopic apparatus is incorporated with an intracranial pressure monitoring catheter or other intraventricular catheter.

16. A system according to claim 1 wherein the bone is skull bone and the operating location is epidural.

17. A system according to claim 1 further comprising an infusion lumen and a source of infusate connectable to the infusion lumen and useable to infuse infusate while measurements are being obtained using the optical spectroscopic apparatus or intermittently at times when measurements are not being obtained by the optical spectroscopic apparatus.

18. A system according to claim 17 further comprising apparatus useable to stop infusion of infusate at a time when measurements are being obtained by the optical spectroscopic apparatus.

19. A system according to claim 17 wherein the infusion lumen extends through a cannula that is insertable into said full-thickness opening, and wherein the infusion lumen is configured for both introduction of the optical spectroscopic apparatus to said operating location and infusion of the infusate.

20. A system according to claim 17 wherein the infusion lumen extends through a cannula that is insertable into said full-thickness opening, and wherein the cannula farther comprises a second lumen configured for introduction of the optical spectroscopic apparatus to said operating location.

* * * * *

UNITED STATES PATENT AND TRADEMARK OFFICE
CERTIFICATE OF CORRECTION

PATENT NO. : 10,716,499 B1
APPLICATION NO. : 15/079020
DATED : July 21, 2020
INVENTOR(S) : Gary A. Freeman Page 1 of 2

It is certified that error appears in the above-identified patent and that said Letters Patent is hereby corrected as shown below:

In the Claims

In Column 14, Line 14, In Claim 2:
Delete "from" and insert -- from: --, therefor.

In Column 14, Line 18, In Claim 2:
Delete "anaylte" and insert -- analyte --, therefor.

In Column 14, Line 19, In Claim 2:
Delete "anaylte" and insert -- analyte --, therefor.

In Column 14, Line 25, In Claim 3:
Delete "from" and insert -- from: --, therefor.

In Column 14, Line 25, In Claim 3:
Delete "light and" and insert -- light; and, --, therefor.

In Column 14, Line 39-40, In Claim 7:
Delete "bone and" and insert -- bone; and, --, therefor.

In Column 14, Line 43, In Claim 7:
Delete "an" and insert -- the --, therefor.

In Column 14, Line 57, In Claim 10:
After "wherein" insert -- the --.

In Column 14, Line 62, In Claim 11:
Delete "sternum," and insert -- sternum --, therefor.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,716,499 B1

In Column 16, Line 17, In Claim 20:
Delete "farther" and insert -- further --, therefor.